United States Patent [19]

Grabley et al.

[11] Patent Number: 5,100,921
[45] Date of Patent: Mar. 31, 1992

[54] ANGUCYCLINONES FROM STREPTOMYCETES, A PROCESS FOR THE PREPARATION THEREOF, AND THE USE THEREOF

[75] Inventors: Susanne Grabley, Königstein/Taunus; Joachim Wink, Offenbach; Carlo Giani, Frankfurt am Main; Gerhard Seibert, Darmstadt; Wolfgang Raether, Dreieich; Susanne Dobreff; Axel Zeeck, both of Göttingen, all of Fed. Rep. of Germany

[73] Assignee: Hoechst Aktiengesellschaft, Frankfurt am Main, Fed. Rep. of Germany

[21] Appl. No.: 342,936

[22] Filed: Apr. 25, 1989

[30] Foreign Application Priority Data

Apr. 27, 1988 [DE] Fed. Rep. of Germany ....... 3814217

[51] Int. Cl.⁵ ............................................. A61K 31/12
[52] U.S. Cl. .................................. 514/680; 568/326; 435/64; 435/253.4
[58] Field of Search .......................... 568/326; 514/680

[56] References Cited

U.S. PATENT DOCUMENTS 4,731,468  3/1988  Gesson et al. ................... 568/326
4,945,108  7/1990  Grabley et al. .................. 514/680

FOREIGN PATENT DOCUMENTS 2100783  3/1972  France .

OTHER PUBLICATIONS

Kuntsmann, M. P. et al., J. Organic Chemistry 31: 2920-2925 (1966).
Bowie, J. H. et al., "The Structure of Ochromycinone", Tetrahedron Letters 16:1449-1452 (published 1967) in Great Britain.

Primary Examiner—James H. Reamer
Attorney, Agent, or Firm—Finnegan, Henderson, Farabow, Garrett, and Dunner

[57] ABSTRACT

New angucyclinones with a therapeutic action can be prepared with the aid of a strain of the genus Streptomyces.

3 Claims, No Drawings

ANGUCYCLINONES FROM STREPTOMYCETES, A PROCESS FOR THE PREPARATION THEREOF, AND THE USE THEREOF

DESCRIPTION

It is known that Streptomyces spec. synthesizes under conventional culture conditions an angucyclinone called ochromycinone [Bowie J. H., Johnson A. W. Tetrahedron Letters 16, 1449 (1967)].

It has now been found, surprisingly, that Streptomyces spec. DSM 4357 forms, besides ochromycinone, new angucyclinones with pharmacological, in particular antibiotic, activity.

Hence the invention relates to:

1. A compound of the general formula I,

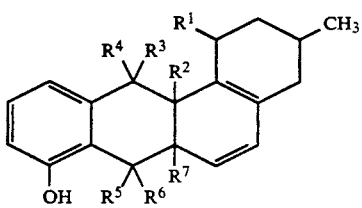

in which, independently of one another,
$R^1$ is hydroxyl or an oxo group,
$R^2$ is hydrogen
$R^3$ is hydroxyl and
$R^4$ is hydroxymethyl or hydrogen or
$R^3$ and $R^4$ together are an oxo group,
$R^5$ is hydroxymethyl or hydrogen,
$R^6$ is hydroxyl or
$R^5$ and $R^6$ together are an oxo group and
$R^7$ is hydroxyl or hydrogen or
$R^2$ and $R^7$ together form a double bond,
as well as the ($C_1$ to $C_5$)-acyloxy compounds derivatized on the hydroxyl groups indicated in the formula I, excepting the compound in which $R^1$ as well as $R^3$ together with $R^4$ as well as $R^5$ together with $R^6$ represent an oxo group, and $R^2$ and $R^7$ together form a double bond.

2. A process for the preparation of the compound of the general formula I as well as of the ($C_1$ to $C_5$)-acyloxy derivatives thereof, which comprises a) cultivating Streptomyces spec. DSM 4357 until the compound of the general formula I accumulates in the culture medium, and b) where appropriate isolating and acylating the compound.

3. The use of the compound of the general formula I, as well as of the ($C_1$ to $C_5$)-acyloxy derivatives thereof, as a therapeutically active substance.

The invention is described in detail hereinafter, especially in its preferred embodiments. The invention is also defined in the patent claims.

The compound of the general formula I can be prepared with the aid of Streptomyces spec. DSM 4357. The strain was deposited in accordance with the conditions of the Budapest Treaty on Jan. 15, 1988, at the Deutsche Sammlung von Mikroorganismen (German Microorganism Collection) under the stated number.

Streptomyces spec. DSM 4357 has the following characteristic features:

| Spore color: | gray |
| --- | --- |
| Spore chain: | divergent spirals |
| Spore surface: | smooth |
| Melanin formation: | negative |
| Pigment formation: | |
| substrate mycelium: | Endo: negative |
| | Exo: violet |
| aerial mycelium: | Endo: negative |
| | Exo: negative |
| Sugar and sugar alcohol utilization: | arabinose, xylose, rhamnose, raffinose, mannitol, fructose, sucrose. |

In place of Streptomyces spec. DSM 4357 it is also possible to use the mutants and variants thereof as long as they are likewise able to produce the compound of the general formula I. Such mutants can be generated in a manner known per se by physical means, for example irradiation, such as with ultraviolet or X-rays, or chemical mutagens such as, for example, ethyl methanesulfonate (EMS), N-methyl-N'-nitro-N-nitrosoguanidine (MNNG) or 2-hydroxy-4-methoxybenzophenone (MOB).

Suitable and preferred carbon sources for the aerobic fermentation are assimilable carbohydrates and sugar alcohols such as glucose, lactose or D-mannitol, as well as carbohydrate-containing natural products such as malt extract. Suitable and preferred nitrogen-containing nutrients are: amino acids, peptides and proteins as well as the degradation products thereof, such as peptones or tryptones, also meat extracts, milled seeds, for example of corn, wheat, beans, soybean or the cotton plant, distillation residues from the production of alcohol, meat meals or yeast extracts, but also ammonium salts and nitrates. The nutrient solution can additionally contain, for example, chlorides, carbonates, sulfates or phosphates of the alkali metals or alkaline earth metals, iron, zinc and manganese as additional inorganic salts.

The formation of the compound of the general formula I takes place especially well in a nutrient solution which contains glycerol in concentrations of 0.5 to 6%, preferably 2-4%, and soybean meal in concentrations of 0.1 to 4%, preferably 0.5 to 2%, in each case based on the weight of the complete nutrient solution.

The fermentation is carried out aerobically, that is to say, for example, submerged with shaking or stirring in shaken flasks or fermenters, where appropriate introducing air or oxygen. The fermentation can be carried out in a temperature range from about 18° to 40° C., preferably at about 25° to 30° C., especially at 28° to 30° C. The microorganism is cultivated under the said conditions until the stationary phase is reached, for about 60 to 120 hours, preferably 70 to 75 hours.

The cultivation is advantageously carried out in several stages, i.e. one or more precultures are initially prepared in a liquid nutrient medium and are then transferred into the actual production medium, the main culture, for example in the ratio 1:10 by volume. The preculture is obtained, for example, by transferring a sporulated mycelium into a nutrient solution and leaving it to grow for about 48 to 72 hours. The sporulated mycelium can be obtained by leaving the strain to grow for about 7 days on a solid or liquid nutrient medium, for example yeast-malt agar.

The progress of the fermentation can be monitored by means of the pH of the culture or of the mycelium volume, by thin-layer chromatography or testing the biological activity.

The angucyclinones of the general formula I are isolated from the culture medium by known methods taking account of the chemical, physical and biological properties of the products. To assay the antibiotic concentration in the culture medium or in the individual stages in the isolation it is possible to use thin-layer chromatography, for example on silica gel with chloroform/methanol as mobile phase, with the amount of antibiotics formed expediently being compared with a calibration solution.

The angucyclinones of the general formula I are present both in the mycelium and in the culture broth. It is therefore expedient for the isolation of the substance to work up both. It is advantageous before the actual working up to separate the mycelium from the culture broth, for example by filtration or centrifugation. The compound of the general formula I can then be isolated from the supernatant or filtrate, expediently in the pH range 2 to 8, preferably at pH values from 5 to 7. The substance can be extracted with conventional agents, for example polar solvents, for example lower alkanols. However, it is advantageous to pass the liquid over an adsorber resin such as, for example, an adsorber based on polystyrene. The elution can then be carried out with a polar solvent, preferably lower alkanols such as, for example, methanol, which are possibly also mixed with water. The solvent can be removed from the eluate by distillation, and the aqueous residue containing the angucyclinones can be dried.

The angucyclinones of the general formula I are colorless amorphous solids which are readily soluble in methanol, acetone, DMSO, dioxane and chloroform but not in water and alkanes. The desired ($C_1$ to $C_5$)-acyloxy derivatives are obtained by base-catalyzed acylation of the hydroxyl groups with an appropriate anhydride.

The compound of the general formula I, as well as the ($C_1$ to $C_5$)-acyloxy derivatives, preferably ($C_1$ to $C_2$)-acyloxy derivatives, can be incorporated in pharmaceutical formulations appropriate for their stability. The antibacterial and antifungal action can be shown in vitro in the agar diffusion test. The angucyclinones additionally exhibit a potent action against protozoa, especially against Trichomonas vaginalis.

The invention is explained in more detail in the examples which follow. Percentage data relate, as in the previous description too, to weight. The Rf values stated below relate to SilG/UV 254+366; 0.25 mm layer thickness from Macherey & Nagel.

EXAMPLES 1.a) Preparation of a suspension of spores of the producer strain:

100 ml of nutrient solution (4 g of yeast extract, 10 g of malt extract, 4 g of glucose, 1 l of tap water, pH before sterilization 7.3) in a 500 ml Erlenmeyer flask are inoculated with the strain DSM 4357 and incubated at 27° C. and 120 rpm on a rotating shaker for 72 hours. Subsequently 20 ml of culture liquid are uniformly distributed in a 500 ml Erlenmeyer flask containing the nutrient medium of the abovementioned composition to which 20 g of agar/l have been added for solidification, and are decanted. The cultures are incubated at 27° C. for 10 to 14 days. The spores which have resulted after this time in one flask are rinsed out with 500 ml of deionized water which contains one drop of a commercially available nonionic surfactant (Triton X100 from Serva), and immediately used further or stored at −22° C.

b) Preparation of a culture or preculture of the producer strain in an Erlenmeyer flask A 500 ml Erlenmeyer flask containing 100 ml of a nutrient solution composed of 2% meat meal, 10% malt extract, 1% calcium carbonate and water ad 100% (pH 7.2 before autoclaving) is inoculated with a culture grown in a slant tube or with 0.2 ml of spore suspension and incubated at 27° C. and 120 rpm in a shaker. The maximum antibiotic production is reached after 72 hours. A 48-hour old submerged culture (5%) from the same nutrient solution suffices to inoculate 10 and 100 l fermenters.

2. Preparation of the angucyclinones

A 10 l fermenter is operated under the following conditions:

Nutrient medium:
  30 g/l glycerol
  2 g/l casein peptone
  1 g/l $K_2KPO_4$
  1 g/l NaCl
  0.5 g/l $MgSO_4.7H_2O$
  5 ml/l trace element solution
Trace elements:
  3 g/l $CaCl_2.2H_2O$
  1 g/l $FeC_6O_7H_5$
  0.2 g/l $MnSO_4$
  0.1 g/l $ZnCl_2$
  0.025 g/l $CuSO_4.5H_2O$
  0.02 g/l $Na_2B_3O_7.10H_2O$
  0.004 g/l $CoCl_2$
  0.01 g/l $Na_2MoO_4. 2H_2O$
  pH 7.2
Incubation time: 72 hours
Incubation temperature: 30° C.
Stirrer speed: 250 rpm
Aeration: 4 l of air/min.

Foam formation can be suppressed by repeated addition of a few drops of ethanolic polyol solution. The production maximum is reached after about 70 hours (pH=5.3). The yields are about 20 mg/l.

3. Isolation of the angucyclinones

After the fermentation of DSM 4357, the culture broth is filtered with the addition of 2% Celite as filtration aid. The mycelium is extracted with acetone, the organic phase is evaporated, and the aqueous residue is added to the culture filtrate. The culture filtrate is passed through an adsorber resin based on polystyrene (XAD2, from Fluka). The effluent is discarded, and the angucyclinones are eluted with methanol/$H_2O$ (80:20). The eluate is distilled. The angucyclinones are present in the distillation residue.

4. Isolation and characterization of the compound

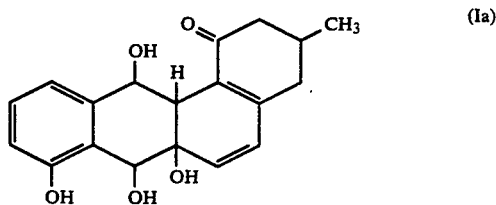

(Ia)

The compound Ia was isolated from the culture filtrate of the Streptomycetes strain DSM 4357. The lyophilisate from a 150 l fermentation was suspended with 10 g of silica gel in a little mobile phase, loaded onto a prepared silica gel column (10×25 cm, silica gel 0.04×0.063 mm) and separated into two fractions with chloroform/methanol (2 1, 20:1; 5 1 gradient to 9:1) under medium pressure:

Fraction 1: 180 g of a mixture of other components with a larger Rf than Ia,

Fraction 2: 2.8 g, Rf=0.58 [chloroform/methanol (9:1, v:v)].

Melting point: 168° C.

IR (KBr): $\gamma$=3400, 3250, 2955, 2905, 2978, 1635, 1595, 1565, 1470, 1300, 1282, 1255, 1020, 1000, 790, 750 cm$^{-1}$.

UV (CHCl$_3$:CH$_3$OH=1:1): $\lambda$ (lg $\epsilon$)=234 (2.4), 286 (2.8) nm. $^1$H NMR (200 MHz, DSMO-d$_6$, 35° C.): $\delta$=9.29 (s 1H, H/D), 7.08 (dd, J=8.0 Hz; 1H), 6.77 (d, J=8.0 Hz; 1H), 6.74 (d, J=8.0 Hz; 1H), 6.24 (d, J=9.0 Hz; 1H), 6.10 (d, J=9.0 Hz; 1H), 5.77 (dd, J=4.0 Hz, J=9.0 Hz; 1H), 5.45 (s; 1H, H/D), 4.96 (d, J =6.0 Hz; 1H, H/D), 4.68 (d, J=6.0 Hz; 1H), 4.63 (d, J=9.0 Hz; 1H, H/D), 3.16 (d, J=4.0 Hz; 1H), 2.6 - 1.95 (m; 5H), 1.03 (d, J=5.5 Hz; 3H) ppm.

$^{13}$C NMR (200 MHz, DMSO-d$_6$): $\delta$=198.1 (C=O), 156.1 (C), 149.4 (C), 140.8 (C), 136.8 (CH), 128.8 (C), 127.8 (CH), 127.4 (CH), 123.1 (C), 120.5 (CH), 113.5 (CH), 71.1 (C), 67.6 (CH), 67.2 (CH), 48.5 (CH), 46.1 (CH$_2$), 37.5 (CH$_2$), 28.2 (CH), 20.3 (CH$_3$) ppm.

EI-MS (70 eV): m/e=310 (M-H$_2$O,>1%), 292 (M-2H$_2$O, 100%),

High resolution: 292.1102 corresponding to C$_{19}$H$_{16}$O$_3$.

Molecular formula: C$_{19}$H$_{20}$O$_5$ (328.3749 g mol$^{-1}$).

5. Preparation and characterization of the di-0-acetyl and tri-0-acetyl compounds of the formula Ia 40 mg (0.12 mmol) of Ia were stirred in 1 ml of pyridine and 1 ml of acetic anhydride at 4° C. for one day. 100 ml portions of toluene were added twice to the reaction mixture, and the solvent was evaporated off in vacuo. Column chromatography (column: 2.5×25 cm) on silica gel (0.064 mm) in chloroform yielded 2 fractions:

Fraction 1: 2.6 mg of tri-0-acetyl-Ia (5%)
Fraction 2: 44 8 mg of di-0-acetyl-Ia (91%).
Di-0-acetyl-Ia:
Melting point=250° C.

Rf = 0.44 (chloroform/methanol = 9:1, v:v),
0.13 (chloroform/methanol = 98:2, v:v).

(on SilG/UV 254+366; 0.25 mm layer thickness, from Macherey & Nagel)

IR (KBr): $\delta$=3440, 2955, 2925, 2875, 1760, 1740, 1625, 1565, 1460, 1410, 1370, 1295, 1230, 1192, 1050, 1020 cm$^{-1}$.

UV (CHCl$_3$):$\lambda$ (lg $\epsilon$)=295 (3.8) nm.

$^1$H NMR (200 MHz, CDCl$_3$): $\delta$=7.5−7.4 (m; 2H), 7.12 - 7.10 (m; 1H), 6.30 (s; 1H), 6.22 (d, J=11.2 Hz; 1H), 6.17 (d, J=9.5 Hz; 1H), 6.12 (dd, J=4.0 Hz, J=6.8 Hz; 1H), 4.57 (s; 1H, H/D), 4.15 (d, J=6.8 Hz; 1H, H/D), 3.29 (m; 1H), 2.7 - 2.45 (m; 2H), 2.26 (s; 3H), 2.3 - 2.1 (m; 3H), 1.96 (s; 3H), 1.06 (d, J=6.0 Hz; 3H) ppm.

$^{13}$C NMR (200 MHz, CDCl$_3$)=201.6 (C=O), 169.9 (C=O), 169.8 (C=O), 151.5 (C), 149.9 (C), 140.3 (C), 134.2 (CH), 130.1 (2×CH), 128.6 (CH), 127.2 (C), 124.0 (C), 122.5 (CH), 70.9 (C), 68.3 (CH), 67.6 (CH), 47.3 (CH$_2$), 39.3 (CH), 38.8 (CH$_2$), 29.1 (CH), 21.0 (2×CH$_3$), 20.9 (CH$_3$) ppm.

EI-MS (70 eV): m/e=352 (M-CH$_3$CO$_2$H, 5%), 334 (M-CH$_3$CO$_2$H-H$_2$O, 11%), 292 (M-2CH$_3$CO$_2$H, 100%).

Molecular formula: C$_{23}$H$_{24}$O$_7$ (412.4516 g mol$^{-1}$).
Tri-0-acetyl-Ia
Melting point=98° C.

Rf = 0.88 (chloroform/methanol = 9:1, v:v),
0.23 (chloroform/methanol = 98:2, v:v).

(on SilG/UV 254+366; 0.25 mm layer thickness, from Macherey & Nagel)

$^1$H NMR (200 MHz, CDCl$_3$): $\delta$=7.83 (d, J=8.0 Hz; 1H), 7.75 (d, J=4.5 Hz; 1H), 7.44 (dd, J=8.0 Hz, J=8.0 Hz; 1H), 7.14 (dd, J=1.2 Hz, J=8.0 Hz; 1H), 6.37 (d, J=9.5 Hz; 1H), 6.34 (s; 1H, H/D), 6.22 (d, J=9.5 Hz; 1H), 2.7 - 2.4 (m; 2H), 2.32 (s, 3H), 2.3 - 2.0 (m; 3H), 1.99 (s; 3H), 1.95 (s; 3H), 1.09 (d, J=6.0 Hz; 3H) ppm.

EI-MS (70 eV): m/e=394 (M-CH$_3$CO$_2$H, 6%), 334 (M-2CH$_3$CO$_2$H, 24%), 292 (M-2CH$_3$CO$_2$H-CH$_3$CO, 100%).

Molecular formula: C$_{25}$H$_{26}$O$_8$ (454.488 g mol$^{-1}$).

6. Isolation and characterization of the compound Ib

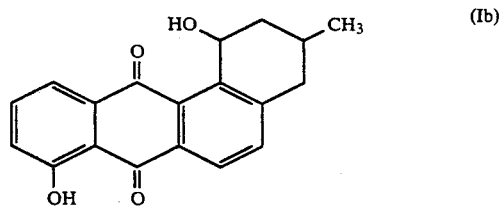

(Ib)

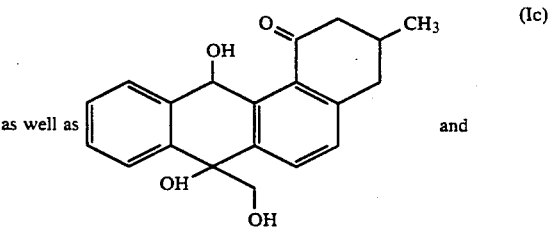

(Ic)

as well as and

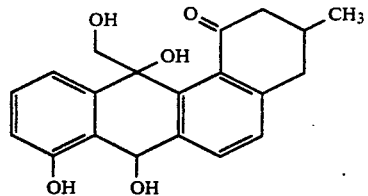

The compounds Ib and c were isolated from the mycelium of the Streptomyces strain DSM 4357. The mycelium from a 150 1 fermentation was extracted twice with 30 1 of acetone each time. The solvent from which the precipitate had been removed by filtration was evaporated in vacuo until the aqueous phase was left. The lyophilisate was suspended in a little mobile phase and separated into two fractions on a column (10×20 cm; silica gel 0.04–0.063 mm) with n-hexane/ethyl acetate (4 1, 4:1; 2 1 gradient to 3:7) under medium pressure:

Fraction 1: 250 mg of Ib Rf=0.35 (n-hexane/ethyl acetate 4:1, v:v),

Fraction 2: 3.5 g of Ic mixed with other components with smaller Rf values than Ib.

Compound Ib

Rf=0.35 (n-hexane/ethyl acetate 4:1, v:v).

IR (IBr): γν=3450, 2950, 2920, 2860, 1700, 1660, 1630, 1580, 1560, 1450, 1370, 1315, 1275, 1250, 1160 cm$^{-1}$.

UV (CH$_3$OH): γ=217, 260, 402 nm.

$^1$H NMR (200 MHz, CDCl$_3$): δ=12.5 (s; 1H, H/D), 8.23 (d, J=8.0 Hz; 1H), 7.79 (dd, J=1.5 Hz, J=8.0 Hz; 1H), 7.65 (dd, J=8.0 Hz, J=8.0 Hz; 1H), 7.53 (d, J=8.0 Hz; 1H), 7.28 (dd, J=1.5 Hz, J=8.0 Hz; 1H), 5.47 (ddd, J=4.5 Hz, J=8.0 Hz; 1H), 4.90 (d, J=4.5 Hz; 1H, H/D), 2.86 (ddd, J=2.5 Hz, J=4.5 Hz, J=17.5 Hz; 1H), 2.65 (dd, J=10.5 Hz, J=17.0 Hz; 1H), 2.39 (tdd, J=2.8 Hz, J=7.2 Hz, J=13.0 Hz; 1H), 2.00 - 1.75 (m; 1H), 1.61 (ddd, J=9.0 Hz, J=11.8 Hz, J=13.0 Hz; 1H), 1.13 (d, J=7.0 Hz; 3H) ppm.

$^{13}$C NMR (200 MHz, CDCl$_3$)=188.2 (C=O), 187.0 (C=O), 161.8 (C), 147.0 (C), 143.4 (C), 136.7 (CH), 135.5 (CH), 134.6 (C), 133.8 (C), 132.3 (C), 126.5 (CH), 124.0 (CH), 120.1 (CH), 115.2 (C), 66.6 (CH), 40.5 (CH$_2$), 39.9 (CH$_2$), 27.5 (CH), 21.5 (CH$_3$) ppm.

EI-MS (70 eV): m/e=308 (M, 100%1, 290 (M-H$_2$O, 5%).

Molecular formula: C$_{19}$H$_{16}$O$_4$ (308.3436 g mol$^{-1}$).

The second fraction from the column chromatography of the mycelium crude product was separated into 3 fractions by the process described above.

Compound Ic: Rf=0.07 (n-hexane/ethyl acetate 4:1, v:v).

Compound Ic:

Melting point=212° C.

Rf=0.71 (chloroform/methanol=9:1, v:v). (on SilG-/UV 254+366; 0.25 mm layer thickness, from Macherey & Nagel)

IR (KBr): γ=3280, 2960, 2875, 1683, 1630, 1590, 1500, 1467, 1350, 1280 cm$^{-1}$.

UV (CH$_3$OH): λ (lg ε)=220 (4.1) 281 (3.7) nm.

$^1$H NMR (200 MHz, acetone-d$_6$): δ=8.5 (m; 1H, H/D), 7.15 - 6.95 (m; 3H), 6.85 - 6.7 (m; 2H), 5.89 (s; 1H), 5.22 (d, J=15.0 Hz; 1H), 4.02 (d, J=15.0 Hz; 1H), 2.99 (s; 1H, H/D), 2.93 (dd, J=6.0 Hz, J =16.5 Hz; 1H), 2.3 - 2.56 (m; 1H), 2.27 (dd, J=11.0 Hz, J=16.5 Hz; 1H), 2.27 (dd, J=3.0 Hz, J =12.5 Hz; 1H), 1.45 (dd, J=12.0 Hz, J=12.5 Hz; 1H), 1.15 (d, J=7.0 Hz; 3H) ppm.

$^{13}$C NMR (200 MHz, acetone-d$_6$):δ=200 (C=O), 154.9 (C), 150.0 (C), 144.5 (C), 139.5 (C), 129.1 (CH), 128.4 (CH), 126.4 (C), 126.1 (C), 124.6 (CH), 120.1 (CH), 118.2 (CH), 115.5 (CH), 108.5 (C), 85.3 (CH), 59.5 (CH$_2$), 42.1 (CH$_2$), 34.7 (CH$_2$), 28.2 (CH), 22.1 (CH$_3$) ppm.

EI-MS (70 eV): m/e=310 (M-CH$_2$O, 23%), 292 (M-CH$_2$OH-H$_2$O, 15%).

Molecular formula: C$_{20}$H$_{20}$O$_5$ (340.3864 g mol$^{-1}$).

We claim:

1. A compound of the general formula I

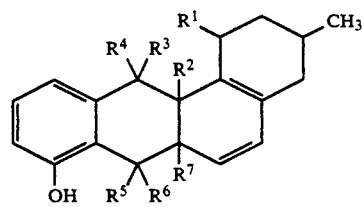

in which, independently of one another,

R$^1$ is hydroxyl or an oxo group,

R$^2$ is hydrogen

R$^3$ is hydroxyl and

R$^4$ is hydroxymethyl or hydrogen or

R$^3$ and R$^4$ together are an oxo group,

R$^5$ is hydroxymethyl or hydrogen,

R$^6$ is hydroxyl or

R$^5$ and R$^6$ together are an oxo group and

R$^7$ is hydroxyl or hydrogen or

R$^2$ and R$^7$ together form a double bond, as well as the (C$_1$ to C$_5$)-acyloxy compounds derivatized on the hydroxyl groups indicated in the formula I, excepting the compound in which R$^1$ as well as R$^3$ together with R$^4$ as well as R$^5$ together with R$^6$ represent an oxo group, and R$^2$ and R$^7$ together form a double bond.

2. A method of treating a human being or an animal for an infectious disease, which comprises: administering to said human being or animal an amount of the compound of formula I as claimed in claim 1 effective to treat said infectious disease.

3. A pharmaceutical composition which comprises:
one or more pharmaceutically acceptable excipients, and
an amount of the compound of formula I as claimed in claim 1 effective to treat or prevent an infectious disease in an animal or patient to whom said composition is administered.

* * * * *